(12) United States Patent
Lima et al.

(10) Patent No.: US 12,011,347 B2
(45) Date of Patent: Jun. 18, 2024

(54) CARBON NANOTUBE SHEET WRAPPING MUSCLES

(71) Applicant: Lintec of America, Inc., Richardson, TX (US)

(72) Inventors: Marcio Dias Lima, Richardson, TX (US); Julia Bykova, Richardson, TX (US); Marilu Guerrero, Richardson, TX (US)

(73) Assignee: LINTEC OF AMERICA, INC., Plano, TX (US)

( * ) Notice: Subject to any disclaimer, the term of this patent is extended or adjusted under 35 U.S.C. 154(b) by 669 days.

(21) Appl. No.: 16/759,130

(22) PCT Filed: Oct. 26, 2018

(86) PCT No.: PCT/US2018/057736
§ 371 (c)(1),
(2) Date: Apr. 24, 2020

(87) PCT Pub. No.: WO2019/084420
PCT Pub. Date: May 2, 2019

(65) Prior Publication Data
US 2020/0345475 A1 Nov. 5, 2020

Related U.S. Application Data

(60) Provisional application No. 62/588,034, filed on Nov. 17, 2017, provisional application No. 62/577,512, filed on Oct. 26, 2017.

(51) Int. Cl.
*B32B 9/00* (2006.01)
*A61F 2/08* (2006.01)
(Continued)

(52) U.S. Cl.
CPC .............. *A61F 2/08* (2013.01); *C01B 32/159* (2017.08); *D02G 3/36* (2013.01); *D02G 3/448* (2013.01);
(Continued)

(58) Field of Classification Search
CPC ....... Y10T 428/30; B82Y 30/00; B82Y 40/00; Y10S 977/742; C01B 32/159
(Continued)

(56) References Cited

U.S. PATENT DOCUMENTS

| 4,620,564 A | 11/1986 | Ekholmer |
| 8,286,413 B2 | 10/2012 | Atkinson et al. |

(Continued)

FOREIGN PATENT DOCUMENTS

| CN | 1530320 | 9/2004 |
| CN | 101931841 | 12/2010 |

(Continued)

OTHER PUBLICATIONS

Taiwanese Office Action dated Nov. 30, 2020 issued in Taiwan (R.O.C.) Patent Application No. 107138071 with a partial English translation.
(Continued)

*Primary Examiner* — Daniel H Miller
(74) *Attorney, Agent, or Firm* — GREENBLUM & BERNSTEIN, P.L.C.

(57) ABSTRACT

A carbon nanotube (CNT) muscle device includes a first CNT yarn. The first CNT yarn includes: one or more first CNT sheets wrapped in the form of a tube; and a first guest actuation material infiltrating the one or more first CNT sheets.

18 Claims, 9 Drawing Sheets

(51) Int. Cl.
*C01B 32/159* (2017.01)
*D02G 3/36* (2006.01)
*D02G 3/44* (2006.01)

(52) U.S. Cl.
CPC ... *A61F 2002/0894* (2013.01); *D10B 2101/122* (2013.01); *Y10T 428/30* (2015.01)

(58) Field of Classification Search
USPC .................................... 428/408; 423/447.1
See application file for complete search history.

(56) References Cited

U.S. PATENT DOCUMENTS

| | | | |
|---|---|---|---|
| 9,784,249 | B2 | 10/2017 | Li et al. |
| 9,903,350 | B2 | 2/2018 | Li et al. |
| 10,480,491 | B2 | 11/2019 | Li et al. |
| 11,143,169 | B2 | 10/2021 | Li et al. |
| 11,149,720 | B2 | 10/2021 | Li et al. |
| 2006/0113510 | A1 | 6/2006 | Luo et al. |
| 2012/0032553 | A1 | 2/2012 | Goyal et al. |
| 2013/0053958 | A1 | 2/2013 | Macossay-Torres |
| 2015/0152852 | A1* | 6/2015 | Li ................ D01H 1/10 60/527 |
| 2015/0219078 | A1 | 8/2015 | Li et al. |
| 2016/0024262 | A1 | 1/2016 | Lu et al. |
| 2018/0073490 | A1 | 3/2018 | Li et al. |
| 2018/0291535 | A1* | 10/2018 | Ridley ............ D06M 11/05 |
| 2020/0088175 | A1 | 3/2020 | Li et al. |
| 2020/0191127 | A1 | 6/2020 | Li et al. |
| 2022/0003221 | A1 | 1/2022 | Li et al. |

FOREIGN PATENT DOCUMENTS

| | | |
|---|---|---|
| CN | 104769834 | 7/2015 |
| CN | 104769834 A | 7/2015 |
| EP | 1 787 575 | 5/2007 |
| EP | 1787575 | 5/2007 |
| EP | 3082248 | 10/2016 |
| EP | 3082248 A2 | 10/2016 |
| JP | 60-159476 | 8/1985 |
| JP | 2010-118609 | 5/2010 |
| JP | 2010-257970 | 11/2010 |
| JP | 2012-39741 | 2/2012 |
| JP | 2012-248670 | 12/2012 |
| JP | 2015-169411 | 9/2015 |
| JP | 2015-533521 | 11/2015 |
| JP | 2017/078461 | 4/2017 |
| JP | 2017-174690 | 9/2017 |
| WO | 2004/109817 | 12/2004 |
| WO | 2006/028019 | 3/2006 |
| WO | 2011/005375 | 1/2011 |
| WO | 2011/005375 A2 | 1/2011 |
| WO | 2014/022667 | 2/2014 |
| WO | 2014/022667 A2 | 2/2014 |
| WO | 2017/058339 | 4/2017 |
| WO | 2017/058339 A2 | 4/2017 |
| WO | 2017/190054 | 11/2017 |

OTHER PUBLICATIONS

Office Action dated Jun. 7, 2021 issued in Japanese patent application No. 2020-523347 with corresponding English translation.
Notice of Allowance dated Mar. 7, 2022 issued in Japanese patent application No. 2020-526932, with an English translation.
Office Action dated Jul. 5, 2021 issued in Japanese patent application No. 2020-526932 with corresponding English translation.
A. Windle and K. Koziol, Continuous Spinning of Carbon Nanotube Fibres: Structure Control and Properties, Seni Gakkaishi, Japan, 2007, vol. 63, No. 11, pp. P-361 to P-364 (see translation of Office Action for relevancy).
International Search Report issued in International Application No. PCT/US2018/057736, mailed on Feb. 28, 2019 (3 pages).
Office Action issued in corresponding Taiwanese Patent Application No. 10920129670, mailed on Feb. 13, 2020 (6 pages).
Written Opinion issued in International Application No. PCT/US2018/057736, mailed on Feb. 28, 2019 (5 pages).
Notice of allowance dated May 17, 2022 issued in Taiwanese patent application No. 107138071 along with corresponding English translation.
Office Action dated Jan. 17, 2022 issued in Japanese patent application No. 2020-523347 with corresponding English translation.
International Preliminary Report on Patentability issued in corresponding International Application No. PCT/US2018/057736 on Apr. 28, 2020 (7 pages).
Japanese Office Action dated Jul. 3, 2023 issued in Japanese patent application No. 2022-063390 along with corresponding English translation.
Decision to grant a patent dated Jan. 22, 2024 issued in Japanese Patent Application No. 2022-063390 along with corresponding English translation.

* cited by examiner

CARBON NANOTUBE SHEET WRAPPING MUSCLES

CROSS REFERENCE TO RELATED APPLICATIONS

This national stage application claims priority to International Patent Application No. PCT/US2018/057736, filed on Oct. 26, 2018, and U.S. Provisional Patent Application Nos. 62/577,512, filed on Oct. 26, 2017, and 62/588,034, filed on Nov. 17, 2017. The contents of these applications are incorporated by reference in their entirety.

BACKGROUND OF INVENTION

Thermally driven torsional actuators based on twisted polymeric and carbon nanotube (CNT) fibers and yarns have a wide range of applications. Artificial muscle actuators, also referred to as artificial muscle devices, comprising twisted and/or coiled polymers have the advantage of low cost, high production volume, and design simplicity. Artificial muscle actuators may have advantages over small motors because of the greatly simplified engineering and lower product costs.

SUMMARY OF INVENTION

In one aspect, embodiments disclosed herein relate to a carbon nanotube (CNT) muscle device that includes a first CNT yarn. The first CNT yarn includes: one or more first CNT sheets wrapped in the form of a tube; and a first guest actuation material infiltrating the one or more first CNT sheets.

In one aspect, embodiments disclosed herein relate to a method of manufacturing a CNT muscle device. The method includes: wrapping one or more first CNT sheets around a core fiber; and infiltrating the one or more first CNT sheets with a first guest actuation material to create a first CNT yarn.

Other aspects and advantages of one or more embodiments disclosed herein will be apparent from the following description and the appended claims.

DETAILED DESCRIPTION

Figure 1:
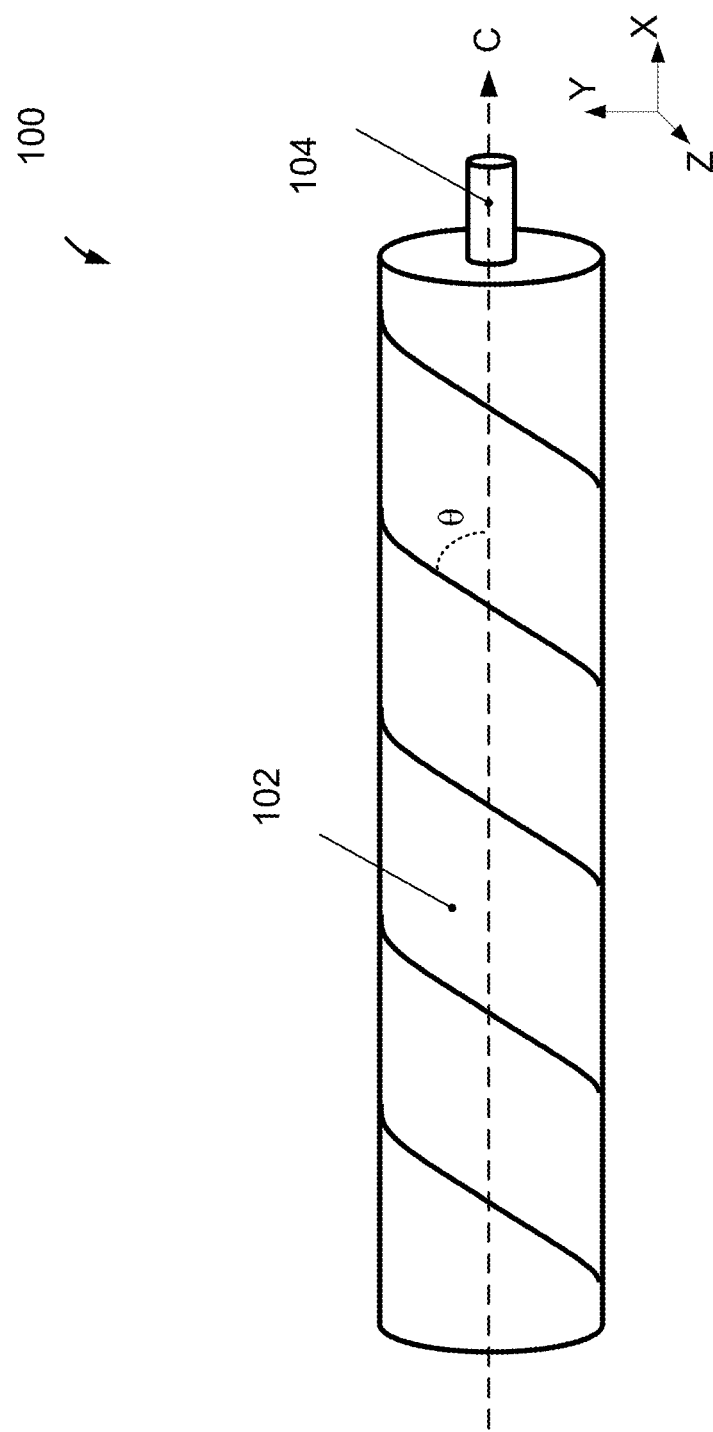
FIG. 1 shows a carbon nanotube (CNT) artificial muscle device in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention relate to a carbon nanotube (CNT) artificial muscle device and a method of manufacturing a CNT artificial muscle device.

FIG. 1 shows the CNT artificial muscle device (hereinafter, CNT muscle device (100)) that includes a CNT yarn (102) disposed around a core fiber (104).

The CNT yarn (102) shown in FIG. 1 includes one or more CNT sheets wrapped around the core fiber (104). Each of the CNT sheets is a thin sheet of a plurality of CNTs disposed next to each other. In one or more embodiments, the CNT sheets may be 0.2 mm wide or more.

In one or more embodiments, the CNT sheets may be wrapped to create a bias angle "θ" with respect to a central access "C" of the CNT muscle device (100). For example, a bias angle of 0° corresponds to CNT sheets oriented parallel to C, and a bias angle of 90° corresponds to CNT sheets oriented perpendicular to C.

In one or more embodiments, the bias angle may in equation (1) below:

$$\theta = \tan^{-1}(2\pi r T) \quad (1)$$

In equation (1), "r" is the radial distance between CNT sheets and C, and "T" is the number of twists (turns) per meter.

In one or more embodiments, the core fiber (104) may be any fiber that has a mechanical strength (i.e., stiffness) chosen based on design or functionality of the CNT muscle device (100). For example, if the core fiber (104) is made of a stiff material, the mechanical strength of the CNT muscle device (100) may be increased, but flexibility of the CNT muscle device (100) may be hindered.

In one or more embodiments, the core fiber (104) may be from, but not limited to, various polymer fibers, metal wire, carbon fiber, glass fiber, basalt Examples of the core fiber include, but are not limited to, fiber, optical fiber, natural fibers/yarns, another CNT yarn, or tows and plies thereof. CNT yarns (e.g., the CNT yarns disclosed in the embodiments herein) may be used as the core fiber because the CNT yarns may have good mechanical strength and good flexibility.

In one or more embodiments, in case the core fiber (104) is a metal wire, the core fiber (104) may be, but not limited to, a metal wire such as tungsten, copper, or a braid of metals. The metal wire may provide mechanical strength (i.e., stiffness) to the CNT muscle device (100), and may provide a highly conductive pathway. This highly conductive pathway may be used to actuate or anneal the CNT muscle device (100).

In one or more embodiments, the diameter of the core fiber (104) may be chosen based on a desired tensile strength and/or stiffness of the CNT muscle device (100).

Figure 2:
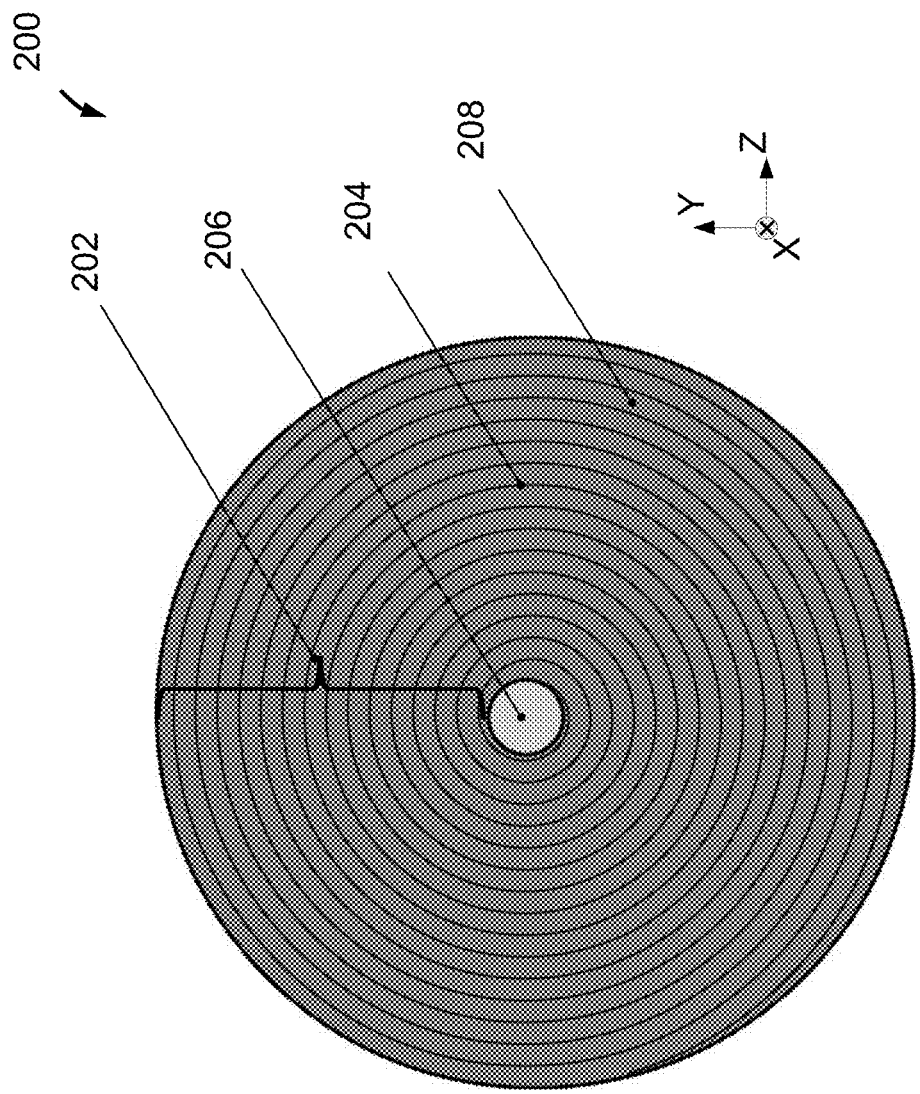
FIG. 2 shows a cross-sectional view of a CNT artificial muscle device in accordance with one or more embodiments of the invention.

FIG. 2 shows a cross-sectional view of the CNT muscle device (200) that includes a core fiber (206) and a CNT yarn (202) disposed around the core fiber (206). The CNT yarn (202) includes one or more CNT sheets (204) wrapped around the core fiber (206) and a guest actuation material (208) infiltrated the CNT sheets (204). In one or more embodiments, the guest actuation material (208) may be infiltrated into the entirety of the CNT sheets (204). In other embodiments, the guest actuation material (208) may be infiltrated into a portion of the CNT sheets (204)

For simplicity, FIG. 2 shows the CNT sheets (204) and the guest actuation material (208) as distinct layers adjacent to each other. However, the CNT sheets (204) and the guest actuation material (208) may be constructed to form highly porous CNT layers with the guest actuation material (208) infiltrated in gaps between the CNT sheets (204) and thus, may not be distinct. These features and any cavities in the CNT layers may have dimensions in the range of nanometers to a few microns (m).

In one or more embodiments, for better infiltration of the guest actuation material (208) into the CNT sheets (204), the guest actuation material (208) may be applied to the CNT sheets (204) while the wrapped CNT sheets (204) are under a vacuum. After applying the guest actuation material (208), the vacuum is removed and the guest actuation material (208) will be sucked into the CNT sheets (204). This is referred to as vacuum-assist infiltration hereinafter.

In one or more embodiments, the core fiber (206) may be a coiled spring (i.e., coiled-spring fiber). In one or more embodiments, an advantage of the coiled-spring fiber may be to better allow the suction of the guest actuation material (208) into inner layers of the CNT sheets (204) (i.e., layers that are closer to the core fiber (206)).

In one or more embodiments, upon powering (i.e., heating) the CNT muscle device (200), the CNT muscle device (200) actuates, which means that the CNT muscle device (200) moves (e.g., rotates, bends, stretches, or contracts) in response to powering the CNT muscle device (200). In one or more embodiments, the actuation of the CNT muscle device (200) is driven by a volume change (i.e., expansion or contraction) of the guest actuation material (208). For example, upon heating the guest actuation material (208), the guest actuation material (208) may expand. Because, although the CNT sheets (204) are flexible, they resist against being stretched and, thus, the bias angle of the CNT sheets (204) may provide rotational and/or tensile movement directions to the volume change of the guest actuation material (208) and cause the actuation.

In one or more embodiments, the CNT muscle device (200) actuates if the CNT muscle device (200) comprises 5 wt % CNT sheets (204) (or CNTs) and 95 wt % guest actuation material (208) so that CNT muscle device (200) would have low tensile strength. However, one of skilled in the art will recognize that the volume percentage or mass percentage of the CNT sheets (204) and the guest actuation material (208) may be chosen based on a preferred design or functionality of the CNT muscle device (200).

In one or more embodiments, an effective way of powering the guest actuation material (208) is by heating the guest actuation material (208) via the CNT sheets (204) through resistive heating. However, the CNT muscle device (200) may be powered with other methods such as power induction, photo absorption, chemical reactions, etc.

In one or more embodiments, other conductive materials (e.g., a metallic wire, a CNT wire, graphene) may be wrapped around the CNT muscle device (200) to heat the guest actuation material (208).

In one or more embodiments, the guest actuation material (208) may be selected based on, but not limited to, its ability to infiltrate the CNT sheets (204), melting point, biocompatibility, chemical resistance, extreme temperature resistance (i.e., durability in hot/cold conditions), or thermal expansion of the guest actuation material (208).

In one or more embodiments, a silicone-based rubber may be used as the guest actuation material (208) because the silicone-based rubber may withstand high temperatures and may not squeeze out of the CNT yarn (202) when heated. In one or more embodiments, the guest actuation material may be Sylgard 184 silicone-based rubber. In one or more other embodiments, the guest actuation material (208) may be paraffin wax.

In one or more embodiments, the guest actuation material (208) may expand uniformly when heated. In one or more embodiments, the guest actuation material (208) may expand radially. As thermal expansion coefficient of the guest actuation material (208) increases, the maximum amount of actuation (actuation capability) of the CNT muscle device (200) may increase as well. In one or more embodiments, softer guest actuation material (208) may provide greater actuation, but a less mechanically strong CNT muscle device (200).

In one or more embodiments, the CNT yarn (202) may include other materials as well. For example, the guest actuation material (208) may include, but not limited to, elastomers (e.g., silicone-based rubber, polyurethane, styrene-butadiene copolymer, and natural rubber), fluorinated plastics (e.g., perfluoroalkoxy alkane (PFA), polytetrafluoroethylene (PTFE), and fluorinated ethylene propylene (FEP)), aramids, (e.g., Kevlar and nomex), epoxies, polyimides, and paraffin wax.

In one or more embodiments, the core fiber (206) may have a thermal expansion coefficient less than thermal expansion coefficient of the guest actuation material (208). In one or more embodiments, the core fiber (206) may not expand noticeably.

In one or more embodiments, the cross-sectional area of the core fiber (206) may be less than 10% of the total cross-sectional area of the device CNT muscle device (200) and may be less than 1% of the total cross-sectional area of the CNT muscle device (200).

Figure 3A:
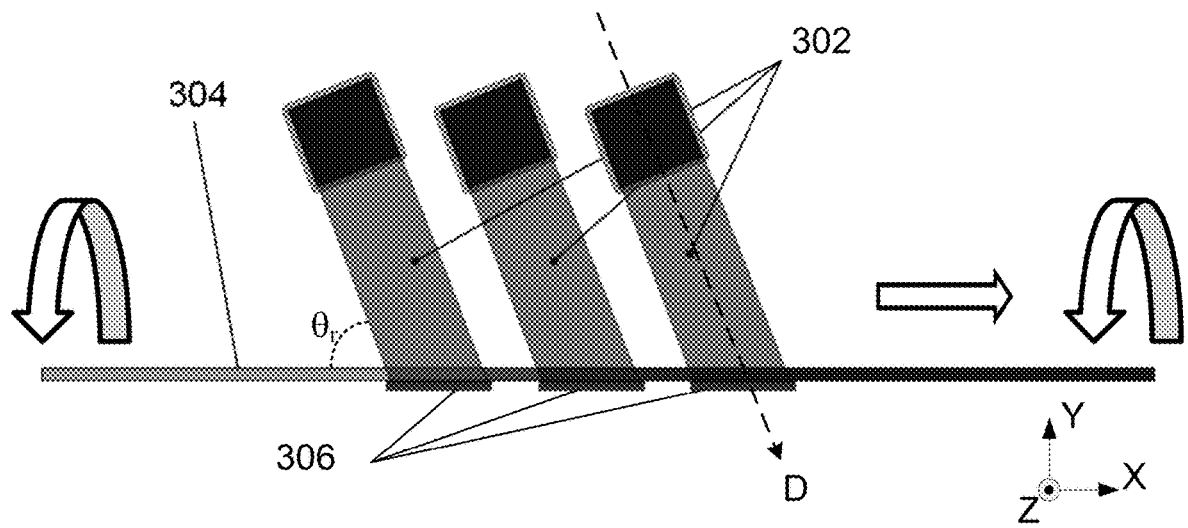
FIGS. 3A and 3B show wrapping CNT sheets of a CNT artificial muscle device in accordance with one or more embodiments of the invention
Figure 3B:
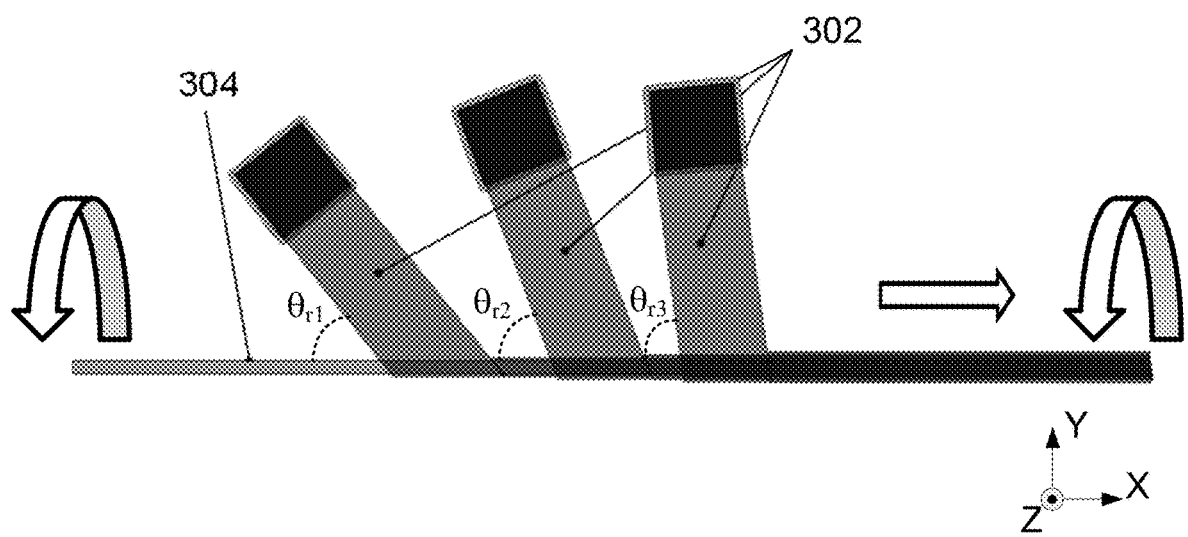

FIGS. 3A and 3B show how the CNT sheets may be wrapped around the core fiber. In FIGS. 3A and 3B, three CNT sheets (302) are disposed on the core fiber (304). The CNT sheets (302) are spaced from each other so that each CNT sheet (302) may form a CNT layer. Upon rotating (shown by the rotational arrows) and pulling (shown by the straight arrows) the core fiber (304) simultaneously, the CNT sheets (302) are wrapped around the core fiber (304) to create three consecutive CNT layers in the entire length of the core fiber (304).

In one or more embodiments, a 15-mm wide CNT sheet (302) may be wrapped ten times around a core fiber (304) that is 1 m in length.

In one or more embodiments, each CNT sheet (302) may be wrapped over itself multiple times to create a stack of CNT sheets (302) in which the CNT sheets (302) may become inseparable and cannot be unwrapped.

In one or more embodiments, the CNTs in each of the CNT sheets (302) may be aligned with each other and may be aligned in a direction along the length of the CNT sheet (302) shown by "D" in FIG. 3A.

In one or more embodiments, the number of CNT sheets (302) may be more or less than three. Also, one CNT sheet (302) can be wrapped around the core fiber (304) multiple times. For example, by moving the rotating core fiber (304) back and forth in a direction along the X axis, one CNT sheet (302) can be wrapped around the core fiber (304) multiple times.

In one or more embodiments, the angle "$\theta_r$" of the CNT sheets (302) with respect to the core fiber (304) is the same as the bias angle "$\theta$" of the CNT sheets shown in FIG. 1 and discussed above.

In one or more embodiments, upon wrapping the CNT sheets (302), there may be a natural drift in $\theta$ toward 90°. In one or more embodiments, by pulling the CNT sheets (302) for a tighter wrapping, the drift in $\theta$ can be reduced or eliminated. In one or more embodiments, the pulling speed and the diameter of the core fiber (304) depend on a desired $\theta$.

CNT sheets (306) may be fluffy. So, as shown in FIG. 3A, a compressing tool (306) may be used to press the CNT sheets (302) to the core fiber (304). In one or more embodiments, the compressing tool (306) may be a blade or a Teflon rod. However, the compressing tool (306) may be anything else based on a preferred manufacturing of the CNT muscle device.

FIG. 3B shows that each of the angles "$\theta_{r1}, \theta_{r2}, \theta_{r3}$" that the CNT sheets (302) make with the core fiber (304) may be adjusted so the CNT layers made by the CNT sheets (302) may have different bias angles with respect to each other. For example, in FIG. 3B, $\theta_{r3}$, which is the bias angle of the outer CNT layer, is closer to 90° than $\theta_{r1}$ and $\theta_{r2}$ that are the bias angles of the CNT layers underneath the outer CNT layer. According to this example, in one or more embodiments, an advantage of the method shown in FIGS. 3A and 3B is that the bias angles of the CNT layers may be precisely controlled as a function of radius.

In one or more embodiments, the bias angle of each of the CNT layers may vary across the length of the core fiber (304). For example, $\theta_r$ may vary while the core fiber (304) moves along X axis.

In one or more embodiments, an advantage of the method shown in FIGS. 3A and 3B is that the CNT sheets (302) may be wrapped at any desired angle. For example, the CNT sheets (302) may be wrapped to provide bias angles of more than 80° for the CNT sheets without coiling the CNT muscle device. However, wrapping the CNT sheets (302) without a core fiber (304) may coil the CNT muscle device such that the CNT muscle device is no longer linear but twisted into a helical pattern. This coiling effect is also known in the art as writhe. The coiling effect for wrapping the CNT sheets (302) without a core fiber (304) may be more likely to occur at lower bias angles.

In other embodiments, the bias angle may increase or decrease as a function of radial distance from the core fiber (304). Thus, it may be advantageous to increase the number of CNT layers so that the bias angle from one CNT layer to another CNT layer can change more smoothly.

In one or more embodiments, while wrapping one CNT sheets (302), by keeping the pulling speed of the core fiber (304), the diameter of the core fiber (306) across the length of the core fiber (306), and $\theta_r$ constant, the bias angle of the CNT sheets (302) across the length of the core fiber (306) may be constant. Alternatively, in other embodiments, changing any of these parameters may vary the bias angle of the CNT sheets (302) across the length of the core fiber (306).

In one or more other embodiments, the CNT sheets (302) may be wrapped such that alternating CNT layers may have alternating bias angles. For example, the bias angles may alternate between +45° and −45°.

Figure 4A:
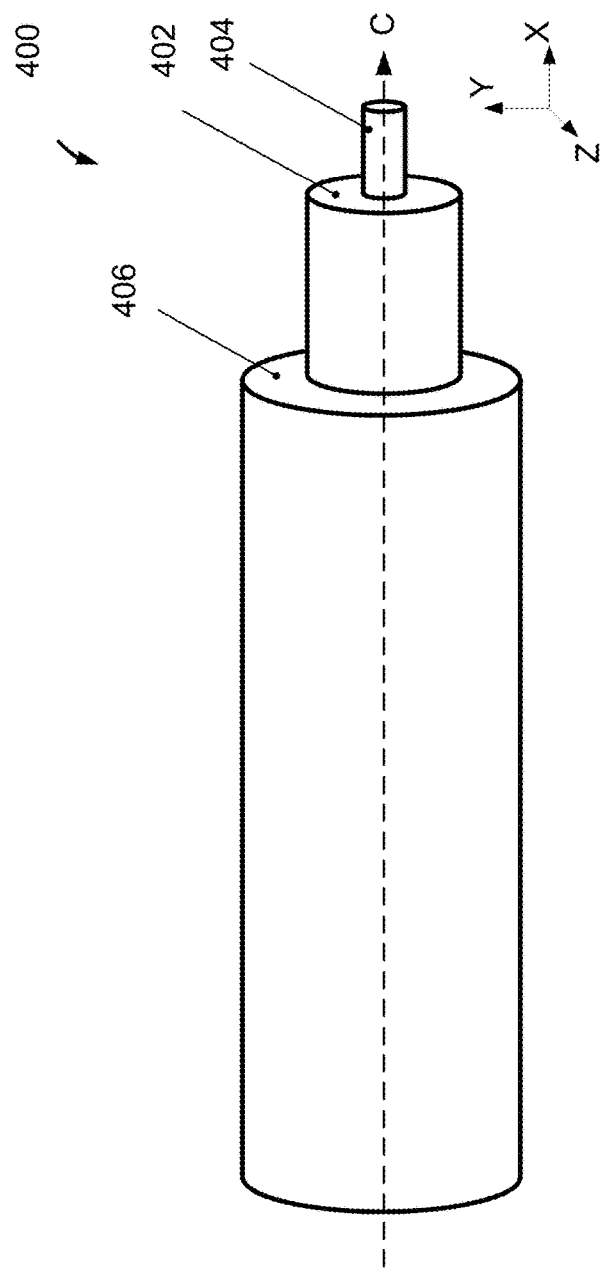
FIGS. 4A and 4B show CNT artificial muscle devices in accordance with one or more embodiments of the invention.
Figure 4B:
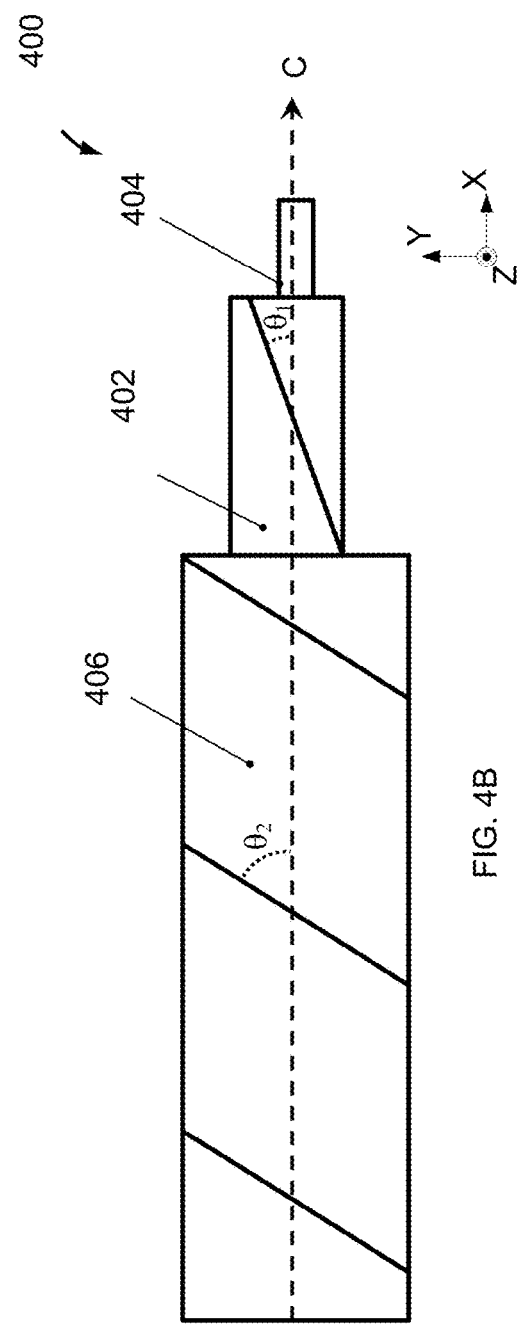

In one or more embodiments, in accordance with FIGS. 4A and 4B, the CNT muscle device may include a plurality of CNT yarns that have different actuation properties. For example, a CNT muscle device (400) that includes a first CNT yarn (402) disposed around a core fiber (404) and a second CNT yarn (406) disposed around the first CNT yarn (402).

In one or more embodiments, the first and the second CNT yarns (402, 406) may have different type or amount of the guest actuation material, different amount of the CNT sheets, different thicknesses, different bias angles, etc., that may determine actuation forces of the first and the second CNT yarns (402, 406). For example, as shown in FIG. 4B, the bias angle of the first CNT yarn "$\theta_1$" and the bias angle of the second CNT yarn "$\theta_2$" may be different (e.g., $\theta_1$ may be smaller than $\theta_2$).

In one or more other embodiments, $\theta_1$ may be 10° and $\theta_2$ may be 70°. In one or more embodiments, $\theta_1$ may be 30° and $\theta_2$ may be 60°. In one or more embodiments, $\theta_1$ may be 60° and $\theta_2$ may be 30°.

In one or more embodiments, a smaller $\theta_1$ with respect to $\theta_2$ may provide more actuation forces for the first CNT yarn (402) with respect to the second CNT yarn (406). However, there may be other factors such as amount and type of the guest actuation material, thicknesses, or amount of the CNT sheets of the first and the second CNT yarns (402, 406) that determine the relative actuation forces of the first and the second CNT yarn (402, 406). For example, in one or more embodiments, one of the first and the second CNT yarns (402, 406) may be incorporated without a guest actuation material. A CNT yarn with no guest actuation material may not provide an actuation force; however, it may provide mechanical strength for the CNT muscle device (400).

In one or more embodiments, it may be advantageous to wrap the CNT sheets at a bias angle of approximately 54.73°. This angle is determined using the single helix model described in "Torsional carbon nanotube artificial muscles" by Javad Foroughi et al. in Science 334.6055, pages 494-497, published in 2011. A single helix is a material that is uniformly twisted in form of a uniform helix. The single helix model is a basic model that works only for a single helix (or one layer) and functions as a good first approximation of the actuation mechanism.

In one or more embodiments, if the CNT yarn allows for a small length increase under a small tension across the length of the CNT yarn and allows for rotation, and if the bias angle is below ~54.73°, upon expansion of the guest actuation material, the CNT yarn tends to untwist. However, when the bias angle is above ~54.73°, the twist of the CNT yarn increases. In one or more embodiments, the former case (the bias angle below ~54.73°) may give a higher actuation than the latter case (the bias angle above ~54.73°), especially in the CNT muscle devices that consist of many layers of CNT yarns with various bias angles.

Figure 5:
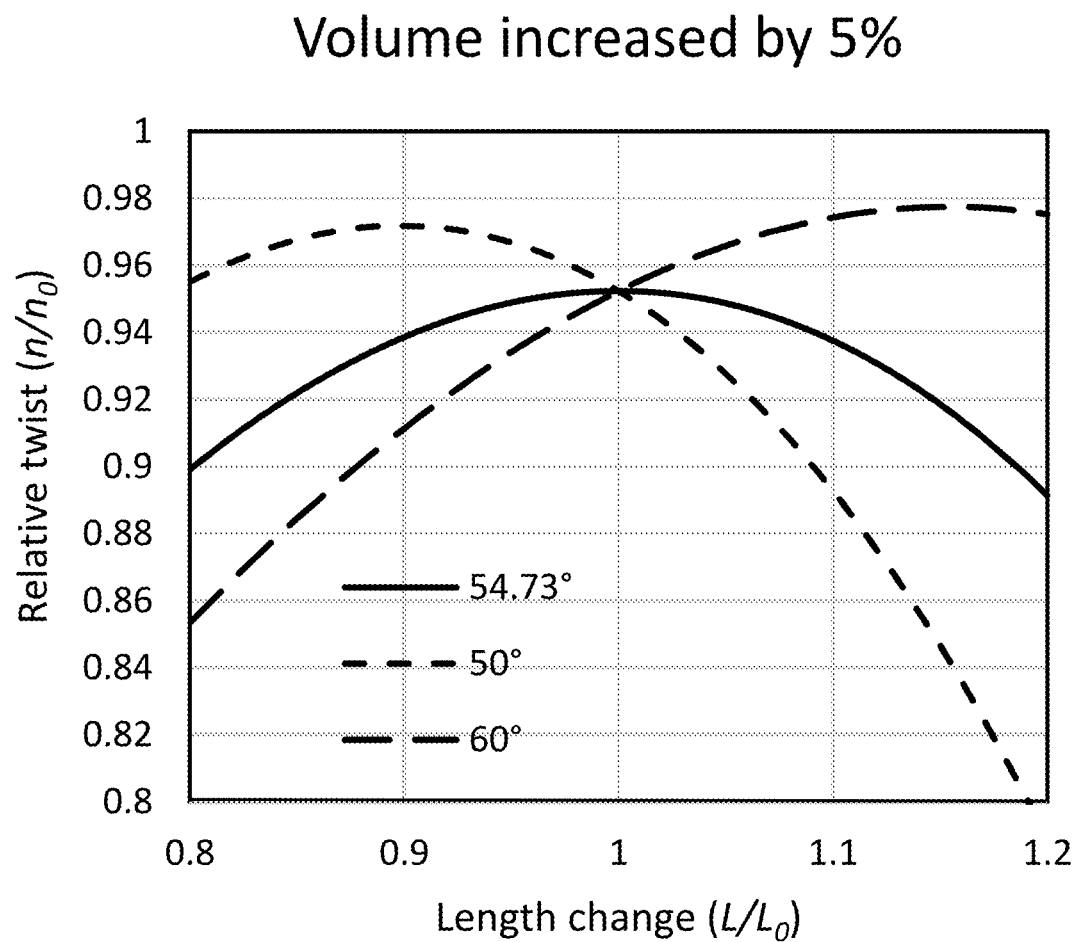
FIG. 5 shows a graph in accordance with one or more embodiments of the invention.

FIG. 5 shows an example of the single helix model when the volume of the guest actuation material increases by 5%. Under a small tension, the length "L" of the CNT yarn (e.g., the length of the CNT yarns (100, 200, 400) in FIGS. 1, 2, and 4A-4B along X axis) may increase from an initial length "$L_0$" so that the length change "$L/L_0$" on the horizontal axis of the graph is greater than 1 If the bias angle is 50° (short-dashed line), which is less than ~54.73°, the relative twist ($n/n_0$) decreases relative to the 54.73° bias angle case (solid line). If the bias angle is 60° (long-dashed line), which is greater than 54.73°, the relative twist ($n/n_0$) increases relative to the 54.73° bias angle case (solid line). Here, n is the twist of the CNT yarn after expansion of the guest actuation material (i.e., upon actuation) and $n_0$ is an initial twist of the CNT yarn before the expansion, which may be the twist when the CNT yarn was manufactured.

In one or more embodiments, it may be advantageous to wrap one or more CNT layers around the core fiber, with no bias angle being larger than 54.73°. In other embodiments, the bias angle may increase or decrease monotonically as a function of radial distance from the core fiber. The bias angle may increase or decrease to a maximum bias angle of 54.73°.

In one or more embodiments, the core fiber may be torsion-free because the core fiber may not be required to create actuation forces.

In one or more embodiments, the bias angle of the CNT yarn may be adjusted to provide the desired combination of actuation and strength of the CNT muscle device. In one or more embodiments, beyond an optimal bias angle (i.e., the bias angle corresponding to maximum actuation (e.g., 54.73°)), the greater the bias angle results in weaker actuation forces of the CNT yarn. In one or more embodiments, the optimum bias angle may not be 54.73°.

In one or more embodiments, in the CNT sheets, CNTs may be aligned across the length of the CNT sheets. In these embodiments, because CNTs are strongest along their length, the CNT sheets are also strong along their bias angle. Thus, relative mechanical strength of the CNT muscle device in directions along the length of the CNT muscle device (e.g., along X axis in FIGS. 1, 2, and 4A-4B) (i.e., longitudinal strength) and perpendicular to the length of the CNT muscle device (i.e., radial strength) depends on the bias angle of the CNT yarn. For example, bias angles closer to 90° provide more radial strength and less longitudinal strength, and vice versa for bias angles closer to 0°.

In one or more embodiments, the strength of the artificial muscle device may depend not only on the bias angle of the CNT yarn but also the strength and diameter of the core fiber, any treatments done to the CNT sheets or the guest actuation material, additional guest materials aside from the guest actuating material, etc.

In one or more embodiments, the CNT yarn may be reinforced to increase mechanical strength of the CNT muscle device against rupture. However, reinforcing the CNT yarn may decrease actuation of the CNT muscle device.

Figure 6:
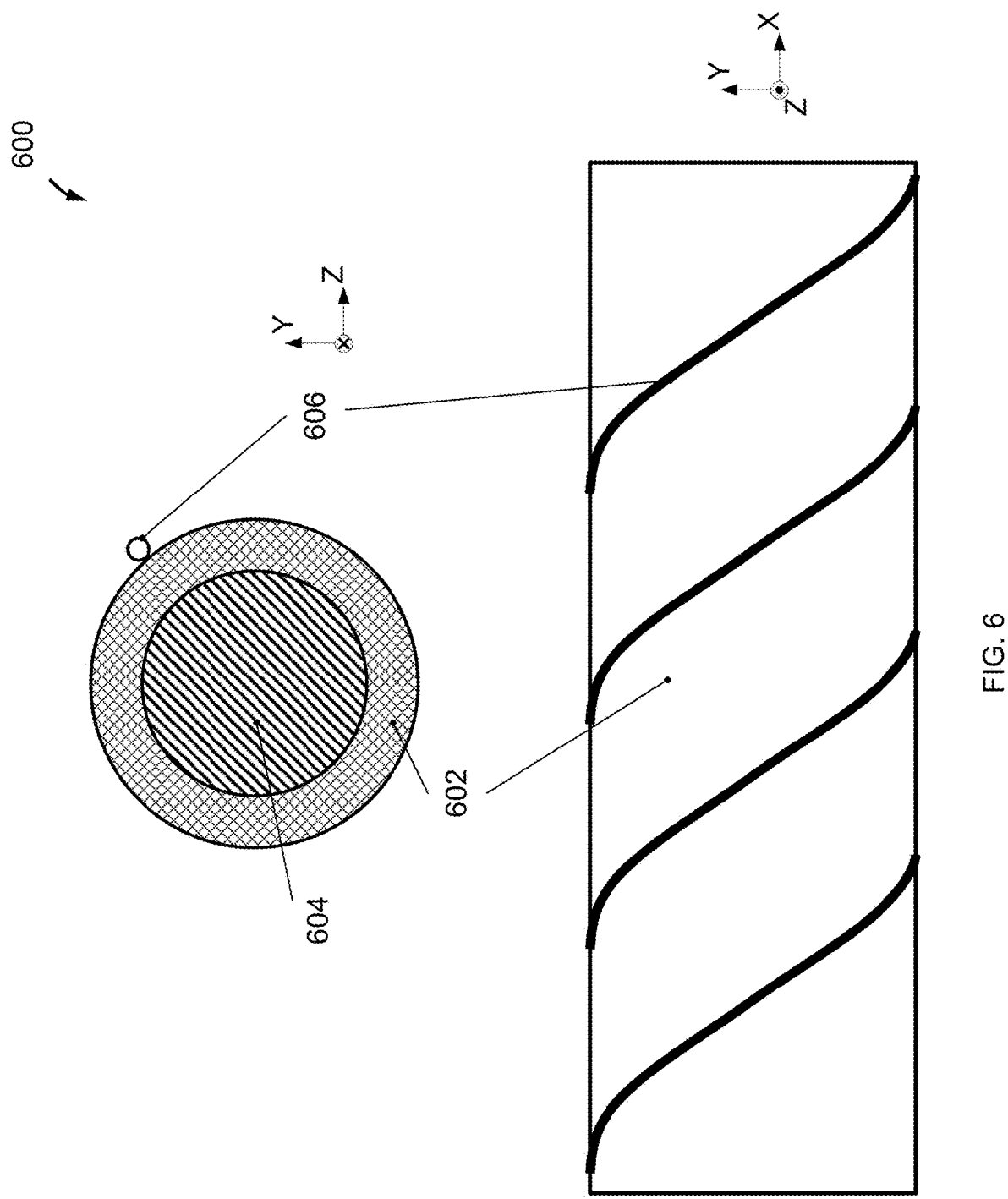
FIG. 6 shows a cross-sectional view and a side-view of a CNT artificial muscle device in accordance with one or more embodiments of the invention.
Figure 7:
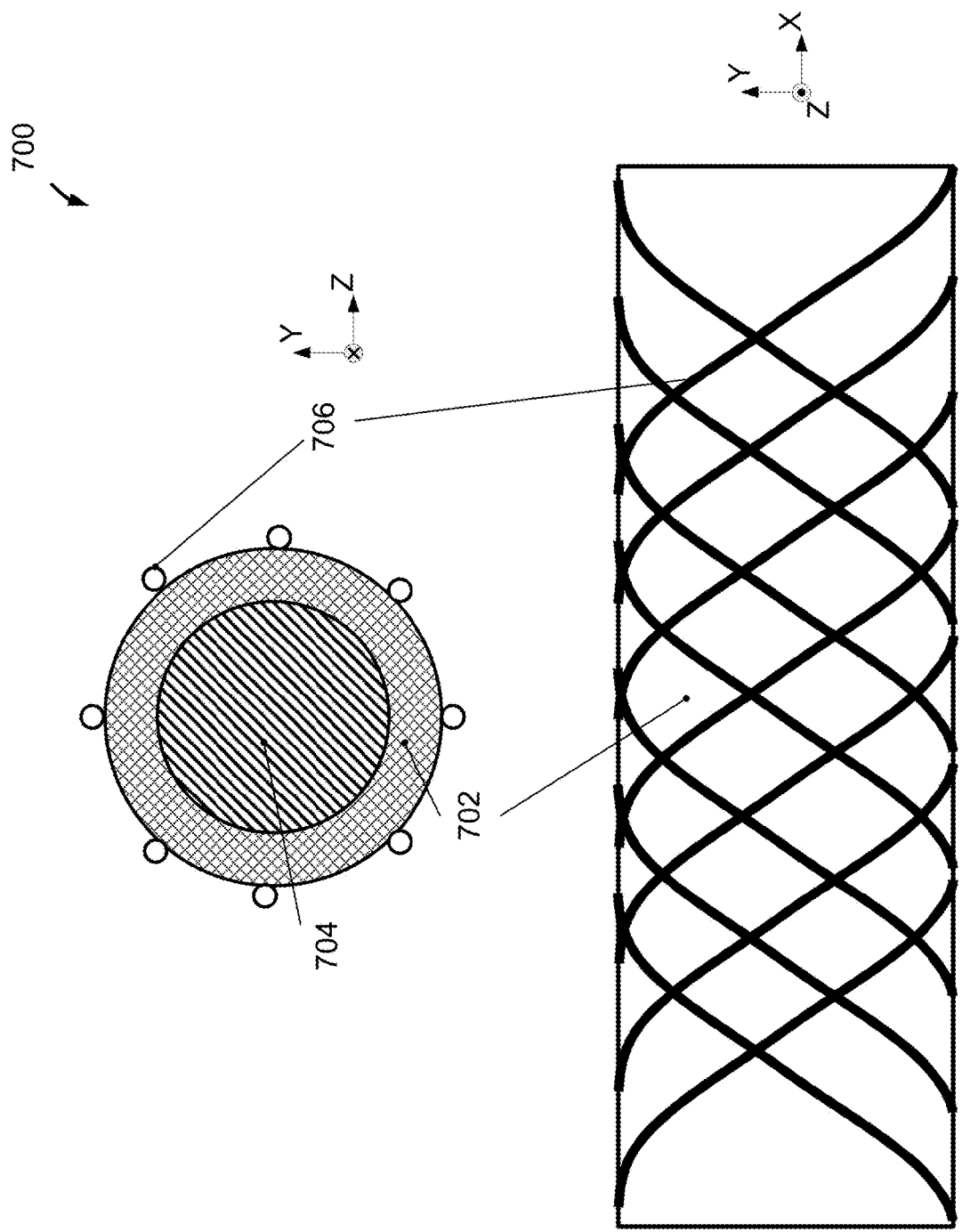
FIG. 7 shows a cross-sectional view and a side-view of a CNT artificial muscle device in accordance with one or more embodiments of the invention.

FIGS. 6 and 7 show cross-sectional views (top of FIGS. 6-7) and side views (bottom of FIGS. 6-7) of CNT muscle devices (600, 700) that include CNT yarns (602, 702) disposed around core fibers (604, 704). To reinforce the CNT yarns (602, 702), reinforcing yarns (606, 706) are wound around the CNT yarns (602, 702). In one or more embodiments, the reinforcing yarns (606, 706) may be CNTs wires (i.e., braided CNTs) that have high torsional strength and good flexibility.

As shown in FIG. 6, the reinforcing yarn (606) may be wound around the CNT yarn (602) such that the reinforcing yarn (606) is aligned to a bias angle. In one or more embodiments, the reinforcing yarn may be wound such that the net bias angle of the reinforcing yarn is 90° (i.e., no bias angle). For example, as shown in FIG. 7, the reinforcing yarn (706) may be braided with alternating bias angles to create the no bias angle condition. In one or more embodiments, the reinforcing yarn may be braided with random orientations and may create the no bias angle condition.

FIGS. 6 and 7, show that the reinforcing yarns (606, 706) are disposed on the outer surface of the CNT yarns (602, 702). However, in one or more embodiments, the reinforcing yarns (606, 706) may be partially or entirely embedded inside the CNT yarns (602, 702). For example, some CNT sheets may be wrapped, then some reinforcing yarns (606, 706) may be wound on the CNT sheets, and then some more CNT sheets may be wrapped to partially or entirely embed the reinforcing yarns (606, 706) in the CNT yarns (602, 702).

In one or more embodiments, the reinforcing yarns (606, 706) may include, but are not limited to, metal wires or springs. An advantage of embedding the reinforcing yarns (606, 706) may be to protect the reinforcing yarns (606, 706) from corrosive agents that may etch the reinforcing yarns (606, 706).

In one or more embodiments, the reinforcing yarns (606, 706) may be wound similarly to wrapping the CNT sheets, in one or more embodiments disclosed herein. For example, the reinforcing yarns (606, 706) may be wound with methods disclosed with reference to FIGS. 3A-3B.

In one or more embodiments, after preparing the CNT muscle device in the above embodiments, the core fiber may be removed. The CNT muscle device that is hollow is referred to a hollow CNT tube.

CNTs may adhere to many materials they contact with. However, in one or more embodiments, the core fiber may be selected to have low surface energy such that the core fiber does not stick to the CNT yarn and may be easily removed from the CNT yarn. For example, in one or more embodiments, the core fiber may be variants of low surface energy silicone or may be coated with silicone. In one or more embodiments, the core fiber is Teflon or has a Teflon coating.

In one or more embodiments, the core fiber may be from a material with a melting point lower than a temperature that damages the CNTs (e.g., ~480 Celsius in Air) or a melting point of the guest actuation material (e.g., ~200 Celsius for silicone). In these embodiments, the core fiber may be removed by being melted and drained. In one or more embodiments, to assist draining the melted core fiber, a pressure differential may be applied across the length of the CNT yarn.

In one or more embodiments, by applying the heat in a vacuum or in an inert gas (e.g., Argon) the damage temperature of the CNTs may increase to over 2000 Celsius.

In one or more embodiments, the core fiber may be from a low melting point metal such as a solder. In one or more embodiments, the diameter of the solder core fiber may be as small as 50 μm.

In one or more embodiments, because CNTs are conductive, the CNT sheets may function as a resistive heater, and the resistive heat may be used to melt the core fiber.

In one or more embodiments, the core fiber is removed by being etched away. For example, the core fiber may be etched away using strong acids or other corrosive agents. CNTs are resistant to most corrosive agents and withstand the etching. For example, the core fiber may be from copper and may be etched away by strong acids such as ferric chloride (FeCl).

In one or more embodiments, the diameter of the copper core fiber may be 5 μm or smaller.

In one or more embodiments, the core fiber may be elastic (e.g., coiled spring, rubber) and stretched such that the diameter of the core fiber decreases and the core fiber separates from the CNT yarn. In these embodiments, after stretching the core fiber, the core fiber may be pulled out of the CNT yarn. In one or more embodiments, the core fiber is a coiled spring that has coils close enough together such that the CNT sheets can be suspended between the pitches of the coils.

In one or more embodiments, when the core fiber is a coiled spring, if the coiled fiber is left inside the CNT yarn, the CNT muscle device may be considered a hollow CNT tube. In one or more embodiments, an advantage of the coiled spring is providing good flexibility of the CNT muscle device.

Figure 8C:
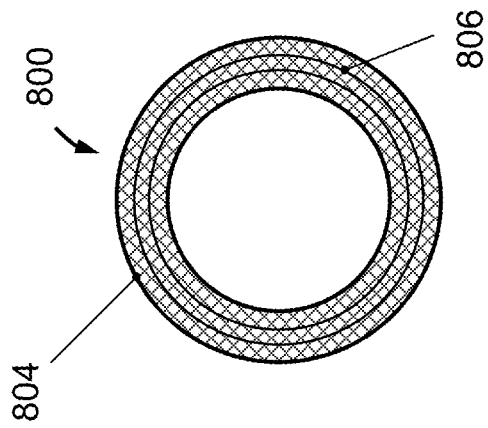
FIGS. 8A-8C show implementation examples in accordance with one or more embodiments of the invention.
Figure 8B:
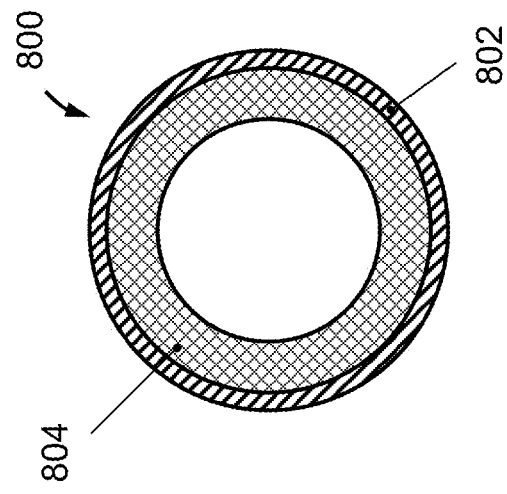
Figure 8A:
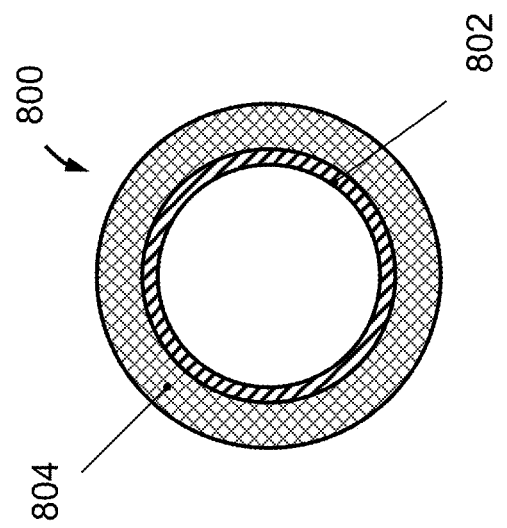

As shown in FIGS. 8A and 8B, the interior surface or the exterior surface of the hollow CNT tube (800) may be coated with a coating material (802).

For example, in one or more embodiments, the coating material (802) may be coated on the core fiber and then the CNT yarn (804) may be wrapped around the coated core fiber. The coating material (802) must adhere to the CNT yarn (804) such that after removing the core fiber, the coating material (802) remains coated on the inner surface of the CNT yarn (804), as shown in FIG. 8A.

In another example in accordance with one or more embodiments, the coating material (802) may coat the outer surface of the CNT yarn (804) with or without the core fiber being removed, as shown in FIG. 8B.

In one or more embodiments, the coating material on the outer surface of the CNT yarn (804) may be the guest actuation material.

In one or more embodiments, the coating material (802) may be cured (e.g., by being annealed). In one or more embodiments, the coating material (802) may be annealed at a temperature below the melting point of the coating material (802).

In one or more embodiments, the CNT sheets may be wrapped such that they contain other materials simultaneously. For example, as shown in FIG. 8C, the CNT sheets may be wrapped such that the CNT yarn (804) contains one or more graphene layers (806). The graphene layers (806) may be, but are not limited to, graphene sheets, graphene flakes, graphene oxide sheets, graphene oxide flakes, or graphene nanoplatelets.

In one or more embodiments, the CNT yarn (804) may include the graphene layers (806) instead of the guest actuation material to prevent a fluid inside the hollow CNT tube (800) escaping from walls of the hollow CNT tube.

In one or more embodiments, to better infiltrate the guest actuation material into the CNT sheets of the hollow CNT tube, a pressure inside the hollow CNT tube may be adjusted to be lower value than a pressure outside the hollow CNT tube so that the guest actuation material may be sucked-in from the outer portion to the inner portion of the hollow CNT tube. For example, a vacuum may be applied to the inner hollow portion (i.e., the portion that is emptied from the core fiber) of the hollow CNT tube.

In one or more embodiments, an advantage of the hollow CNT tube is that although it may have high mechanical strength (e.g., torsional strength), the hollow CNT tube may be designed to have a very small inner diameter. For example, in one or more embodiments, the inner diameter of the hollow CNT tube may be less than 5 μm.

In one or more embodiments, the CNT sheets may be wrapped such that the CNT yarn has a net bias angle that results in the actuation of the hollow CNT tube. Alternatively, in one or more embodiments, the CNT yarn may have no bias angle so the hollow CNT tube does not actuate. For example, randomly oriented CNT sheets produced by filtration methods, sock method, or electrospinning method may be wrapped in accordance with one or more embodiments. In one or more embodiments, the hollow CNT tubes with no bias angle may be used as pipes.

In one or more embodiments, the hollow CNT tube may be reinforced to prevent twisting. For example, the CNT wires disclosed above may be disposed around the hollow CNT actuating device in braid or other patterns in accordance with one or more embodiments.

Figure 9:
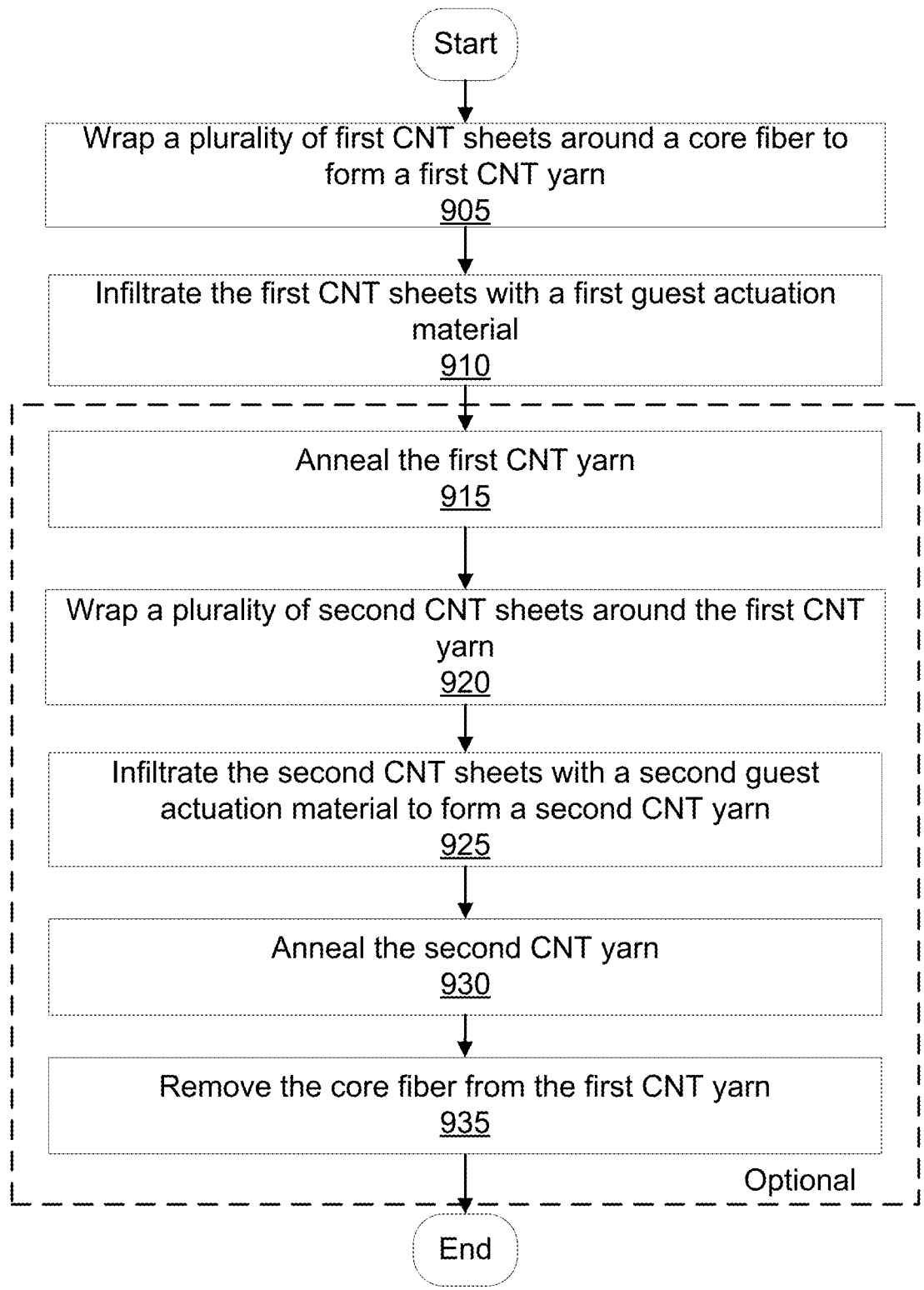
FIG. 9 shows a flowchart in accordance with one or more embodiments of the invention.

FIG. 9 shows a flow chart depicting a method for manufacturing a CNT muscle device. In one or more embodiments, one or more of the steps shown in FIG. 9 may be omitted, repeated, and/or performed in a different order than the order shown in FIG. 9. Accordingly, the scope of the invention is not limited to the specific arrangement of steps shown in FIG. 9.

In STEP 905, one or more CNT sheets (i.e., first CNT sheets) are wrapped around a core fiber. For example, as shown in FIGS. 2 and 3A-3B, the CNT sheets (204, 302) are wrapped around the core fiber (206, 304). In another example, the CNT sheets may be wrapped to create bias angles, such as $\theta$ shown in FIG. 1 and $\theta_1$ and $\theta_2$ shown in FIG. 4B.

In STEP 910, the first CNT sheets may be infiltrated with a first guest actuation material to create a first CNT yarn. For example, the first CNT sheets may be infiltrated with the methods for infiltrating the CNT sheets in accordance with one or more embodiments above.

In STEP 915, the first CNT yarn may be annealed. For example, in one or more embodiments, the first CNT yarn may be annealed in accordance with one or more embodiments above for annealing the CNT yarn.

In STEP 920, more CNT sheets (i.e., second CNT sheets) may be wrapped around the first CNT yarn. For example, as shown in FIGS. 4A-4B, the second CNT yarn (406) is disposed around the first CNT yarn (402). In one or more embodiments, the second CNT sheets may be wrapped according to methods in one or more embodiments above for wrapping the CNT sheets.

In STEP 925, a second guest actuation material may be infiltrated into the second CNT sheets to create a second CNT yarn. For example, as shown in FIGS. 4A-4B, the second CNT yarn (406) disposed around the first CNT yarn (402) is infiltrated with a guest actuation material. In one or more embodiments, the second guest actuation material may be infiltrated according to methods in one or more embodiments above for infiltrating the guest actuation material.

In one or more embodiments, the first and the second guest actuation materials may be from a same material. Alternatively, in other embodiments, the first and the second guest actuation materials may be from different materials.

In STEP 930, the second CNT yarn may be annealed. For example, the second CNT yarn may be annealed in accordance with one or more embodiments above for annealing the CNT yarn. In one or more embodiments, the first and the second CNT yarns may be annealed together. Alternatively, in other embodiments, the first and the second CNT yarns may be annealed differently (e.g., different temperature, annealing time, annealing environment).

In STEP 935, the core fiber may be removed from the first CNT yarn. For example, the core fiber may be removed from the CNT yarn in accordance with one or more embodiments disclosed above.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A carbon nanotube (CNT) muscle device comprising:
a first hollow CNT tube, comprising:
a first set of one or more CNT sheets wrapped to form the first hollow CNT tube with a first hollow CNT tube central axis; and
a first thermal-responsive guest actuation material having a first thermal expansion coefficient infiltrating the first set of one or more CNT sheets,
wherein CNTs in the first set of one or more CNT sheets are aligned to a first bias angle with respect to the first hollow CNT tube central axis, the first bias angle ranging from 10° to 80°, and
wherein, in response to heating, a volume of the first thermal-responsive guest actuation material expands to cause a first rotational and/or tensile actuation of the CNT muscle device.

2. The CNT muscle device according to claim 1, further comprising a core fiber having a second thermal expansion coefficient, wherein the first set of one or more CNT sheets are wrapped around the core fiber.

3. The CNT muscle device according to claim 2, wherein the second thermal expansion coefficient is less than the first thermal expansion coefficient.

4. The CNT muscle device according to claim 1, further comprising:
a second hollow CNT tube, comprising:
a second set of one or more CNT sheets wrapped around the first hollow CNT tube to form the second hollow CNT tube; and
a second thermal-responsive guest actuation material having a third thermal expansion coefficient infiltrating the second set of one or more CNT sheets,
wherein the CNTs in the second set of one or more CNT sheets are aligned to a second bias angle with respect to the first hollow CNT tube central axis, and the degree of the first bias angle is different from a degree of the second bias angle.

5. A method of manufacturing a carbon nanotube (CNT) muscle device, the method comprising:
wrapping a first set of one or more CNT sheets around a core fiber; and
infiltrating the first set of one or more CNT sheets with a first thermal-responsive guest actuation material having a first thermal expansion coefficient to create a first hollow CNT tube having a central axis,
wherein CNTs in the first set of one or more CNT sheets are aligned to a first bias angle with respect to the central axis of the first hollow CNT tube, the first bias angle ranging from 10° to 80°, and
wherein, in response to heating, a volume of the first thermal-responsive guest actuation material expands, the expansion causing a rotational and/or tensile actuation of the CNT muscle device.

6. The method according to claim 5, further comprising:
wrapping a second set of one or more CNT sheets around the first hollow CNT tube; and
infiltrating the second set of one or more CNT sheets with a second thermal-responsive guest actuation material having a third thermal expansion coefficient to form a second hollow CNT tube,
wherein CNTs in the second set of hollow CNT tube are aligned to a second bias angle with respect to the central axis of the first hollow CNT tube, and the degree of the first bias angle is different from a degree of the second bias angle.

7. The method according to claim 5, further comprising annealing the first hollow CNT tube.

8. The method according to claim 5, further comprising removing the core fiber from the first hollow CNT tube.

9. The method according to claim 8, wherein the core fiber is removed by pulling out the core fiber from the first hollow CNT tube.

10. The method according to claim 8, wherein
the core fiber has a lower melting point than the first set of one or more CNT sheets and the first thermal-responsive guest actuation material, and
the core fiber is removed by being melted away from the first hollow CNT tube through heating the core fiber to a temperature above the melting point of the core fiber and below the melting points of the first set of one or more CNT sheets and the first thermal-responsive guest actuation material.

11. The method according to claim 10, further comprising applying different pressures across a length of the first hollow CNT tube to remove the melted core fiber.

12. The method according to claim 8, wherein the core fiber is removed by being chemically etched away.

13. The method according to claim 8, wherein the core fiber is elastic along a length of the core fiber, and the core fiber is removed by being stretched along the length of the core fiber to reduce a diameter of the core fiber and separate the core fiber from an interior surface of the first hollow CNT tube.

14. The method according to claim 8, further comprising:
forming a layer of a first coating on the core fiber before wrapping the first set of one or more CNT sheets,
wherein the first coating adheres to an interior surface of the first hollow CNT tube and remains disposed on the interior surface of the first hollow CNT tube after removing the core fiber.

15. The method according to claim 8, further comprising:
forming a layer of a second coating on an exterior surface of the first hollow CNT tube,
wherein the second coating adheres to and stays on the first hollow CNT tube after removing the core fiber.

16. The CNT muscle device according to claim 4, wherein the first thermal expansion coefficient is different from the third thermal expansion coefficient.

17. The method according to claim 6, wherein the first thermal expansion coefficient is different from the third thermal expansion coefficient.

18. The method according to claim 6, further comprising annealing the second hollow CNT tube.

* * * * *